US006423041B1

(12) United States Patent
Grant

(10) Patent No.: US 6,423,041 B1
(45) Date of Patent: Jul. 23, 2002

(54) CATHETER CADDY

(76) Inventor: Candace Lynn Grant, 5029 Crosswinds Dr., Wilmington, NC (US) 28409

(*) Notice: Subject to any disclaimer, the term of this patent is extended or adjusted under 35 U.S.C. 154(b) by 80 days.

(21) Appl. No.: 09/628,602

(22) Filed: Jul. 31, 2000

(51) Int. Cl.[7] .............................................. A61M 1/00

(52) U.S. Cl. .................... 604/322; D24/122; D24/123; 141/313

(58) Field of Search ......................... 604/317, 322–326; 206/466; D24/121–123; 141/10, 68, 114, 313–317

(56) References Cited

U.S. PATENT DOCUMENTS

| | | | | | |
|---|---|---|---|---|---|
| 2,467,866 A | * | 4/1949 | Smolderen | 248/136 |
| 3,529,599 A | | 9/1970 | Folkman | |
| 4,126,135 A | | 11/1978 | Hinman, Jr. | |
| 4,312,352 A | | 1/1982 | Meisch et al. | |
| 4,447,939 A | | 5/1984 | Taylor | |
| 4,449,969 A | | 5/1984 | Schweizer | |
| 4,496,354 A | | 1/1985 | Steer et al. | |
| 4,534,766 A | | 8/1985 | Steer et al. | |
| 4,850,375 A | * | 7/1989 | Rosenberg | 128/767 |
| D304,239 S | | 10/1989 | Miller | |
| D318,922 S | * | 8/1991 | Kinder | D24/112 |
| 5,549,141 A | * | 8/1996 | Meador et al. | 141/1 |

* cited by examiner

*Primary Examiner*—John G. Weiss
*Assistant Examiner*—Michael Bogart
(74) *Attorney, Agent, or Firm*—MacCord Mason PLLC

(57) ABSTRACT

A carrier is described for supporting a urine drainage bag, enabling the user to carry the drainage bag from place to place and support the bag on a horizontal surface. The carrier is in the form of a molded, one-piece open frame with top, side and bottom walls. The bag is supported on a hook that extends downwardly from the frame top wall. A urine collection receptacle is positioned in the bottom of the frame, with the frame being sized so that the lower end of the bag extends into the receptacle, but above the frame bottom wall when the bag is supported on the hook.

20 Claims, 3 Drawing Sheets

CATHETER CADDY

BACKGROUND OF THE INVENTION (1) Field of the Invention

The present invention relates generally to a carrier for holding a urinary drainage bag, and in particular to a carrier that provides a free-standing support for a urinary drainage bag permitting increased mobility for the user.

(2) Description of the Prior Art

Flexible urinary drainage bags, also known as catheter bags, are commonly used both within and outside a hospital environment by post-operative patients on a temporary basis during recovery, and over the longer term by individuals suffering from urological disorders. Generally, these bags are connected by a drainage tube that has a proximal end attached to an inserted catheter, and a distal end that extends into the upper end of the drainage bag. A collection tube extends from the lower end of the drainage bag for use in emptying the bag.

These bags work well for their intended purposed when used by immobile patients who are confined to a bed or wheelchair. Under such circumstances, the bag is supported on a hook below the level of the patient, so that urine drains under gravity into the bag. However, unless a convenient hook or other hanger is readily available, drainage bags are a substantial deterrent to mobility, and an inconvenience to users that would otherwise be able to move about and perform many normal activities.

The prior art has attempted to address this problem by devising various kinds of flexible urinary drainage bags that are supported by, or form a part of a carrier that is intended to support the bag on a level surface. These devices are said to enable a user to move the carrier and bag to a given location and set the bag on the floor or other surface below the catheter position, enabling the user to function normally up to the length of the drainage tube. In practice, however, these prior art devices include inherent design defects that limit their usefulness.

For example, U.S. Pat. No. 4,126,135 to Hinman, Jr. describes a self-standing drainage bag structure in which a specially designed, flexible drainage bag is mounted between two rigid leaves that are joined to each other at their top edges, with the lower edge of the drainage bag extending below the lower edges of the leaves. A handle extends upwardly from the top edges of the leaves so that the structure can be carried from place to place.

When the Hinman, Jr. structure is lowered onto a horizontal surface, such as the floor, the lower edge of the bag first engages the floor, pushing the bag contents into the area between the leaves. As a result, the leaves expand until the lower edges of the leaves engage the floor. Thus, in the supported position, a large part of the bag's outer surface, as well as the collection tube, is physically in contact with the horizontal surface.

U.S. Pat. No. 4,447,939 to Taylor describes a drainage bag stand that is formed of a plurality of connected shaped rods, including a bent upper rod that forms a handle, a pair of downwardly extending arms that are joined by a back plate, and a pair of legs that extend horizontally outward from the lower ends of the arms. A horizontal reinforcing rod at the upper edge of the reinforcing plate includes hooks that are used to attach a specially designed, flexible drainage bag by inserting the hooks through slots in an attachment strip along the upper edge of the bag.

U.S. Pat. No. 4,449,969 to Schweitzer also describes a frame designed to support a flexible drainage bag on a horizontal surface. The rectangular frame is comprised of an elongated base with posts that extend upwardly from the ends of the base. A horizontal frame member extends between the upper ends of the posts. The frame is sized to accommodate a specially designed, flexible drainage bag of rectangular construction with an attachment slot at each corner. Bosses extend outwardly from each corner of the frame to project into the attachment slots. An elongated support leg with feet at opposed ends is pivotally joined at its center to the center of the base, and is movable between a closed position and an open position, whereby the leg is perpendicular to the base, to support the stand on a horizontal surface.

U.S. Pat. No. 4,496,354 to Steer et al. describes a urine drainage bag and support stand. The frame is formed of a foldable sheet comprised of a back wall, opposed wings that extend from the side edges of the back wall, and a drip tray section formed of foldable bottom, front and side walls. A flexible drainage bag is carried on the front surface of the back wall. The bag is comprised of a rigid back wall that is laminated to the frame back wall, and a flexible front wall, together forming a urine drainage bag that is supported above the drip tray when the sheet is folded into the support frame structure.

All of the above structures, while purporting to provide a stable urine drainage bag stand that facilitates mobility, have one or more disadvantages or design faults that limit their utility. In all instances, a specially designed bag construction is required for use with the stand. In many instances, the bag is positioned so that the bag can be damaged by striking an object during movement from one place to another. Cleaning of the structures in difficult, and bags cannot be readily attached or detached. In a structure like that shown in Hinman, Jr., the bag physically rests on the surface, creating unsanitary conditions, and potential damage to the bag.

With the exception of the Steer et al. structure, none of the designs provide for a means to capture urine in the event of a spill. Even Steer et al. provides only a limited solution to the problem by suggesting a tray that can only be used with a bag that is integrally constructed with the stand. Moreover, since the tray is formed by joining folded blank sections with tabs, its usefulness in holding urine is doubtful.

Thus, there is still an existing need for a stand or carrier that can be used to support a urine drainage bag on horizontal surface, permitting the bag to be carried from one place to another, thereby facilitating the user's mobility.

SUMMARY OF THE INVENTION

The present invention addresses this need by providing an improved urine drainage bag carrier or caddy that can be used to support a drainage bag while the bag is attached by as tube to a user. The carrier enables the bag to be easily carried, and provides a stable support when the bag is placed on a horizontal surface, such as a floor, at the user's destination. At the same time, the carrier protects the bag from damage, and provides means for collecting any urine that might be spilled from the bag or attached tubes.

The carrier described herein is designed for use with a flexible urine drainage bag comprised of first and second flexible plastic sheets that are joined at their periphery, e.g., by heat sealing, to define a urine collection chamber. A drainage tube attachment is fitted to the top of the bag, while a collection tube attachment is fitted to the bottom of the bag. The bag, which is preferably formed of rectangular sheets, also includes an upwardly extending flap that includes a hook-receiving opening to attaching the bag to the stand. The bag has a given width, height, and filled thickness that is relevant to the sizing of the carrier.

The carrier or stand is generally comprised of a generally rectangular frame comprised of a base or bottom wall, first and second opposed side walls that extend upwardly from the opposed ends of the bottom wall, and a top wall that extends between the upper edges of the side walls. A handle is joined to the upper surface of the top wall. Parallel front and back walls extend upwardly from the front and back edges of the bottom wall and are joined to lower sections of the side walls to define a urine drip collection tray in the lower part of the carrier. Feet may be attached to the lower part of the carrier framework to improve stability. A bag attachment, preferably in the from of a hook, extends downward from the top wall between the side walls to attach a drainage bag.

Preferably, the bottom, side, top, front and back walls of the carrier are molded as a single unit, not only for ease of manufacture, but also to provide smooth, continuous surfaces, thereby promoting ease of cleaning and sanitary use. The handle and feet may also form a part of the unitary construction. The hook, depending on the design of the carrier, can be formed as part of the unitary construction, or can be attached later.

In order to achieve the objectives of the present invention, the carrier is sized to accommodate given dimensions of a urine bag to be supported within the interior of the carrier. Utilizing the relationship described herein, the carrier not only provides a stable support for the urine bag when the carrier is placed on a horizontal surface, the carrier also protects the bag from damage from exterior objects. In addition, the carrier is capable of catching any leakage from the bag.

Thus, the carrier is designed to hold a urine bag having a given width, a given height, and a given thickness when filled. More specifically, the bottom wall has a width of at least about the filled thickness of the bag, and a length that is greater than the bag width. Each side wall, at least in its lower portion, also has a width equal to at least about the filled thickness of the bag. The side walls have lower edges that are integral with the outer edges of the bottom wall. The junctures of the side wall lower edges with the bottom wall lower edges are preferably radiused to facilitate cleaning.

The top wall is parallel to the bottom wall, and also has a length greater than the given bag width. Preferably, the top wall has the same length as the bottom wall. The opposed ends of the top wall are joined, preferably with radiused junctures, to the upper edges of the side walls. The top wall has upper and lower surfaces. A carrying handle extends upwardly from, and is integral with the upper surface of the top wall. A hook extends downward from the center of the top wall lower surface equidistant between the carrier side walls, and above the center of the bottom wall. This hook opens toward either to the front or back of the carrier, the front and back being of the same construction, so that a bag can be readily inserted between the side walls and attached to the hook by inserting the end of the hook into a slot or opening in a flap at the top of the bag.

In order to capture any urine that might leak from the bag, the carrier also includes an open-top urine receptacle beneath the bag support area. This receptacle is formed of the bottom wall, the lower portions of the side walls, and front and back walls that have side edges integral with the lower portions of the side walls, and lower edges integral with the front and rear edges of the bottom wall. Due to the integral construction, the walls cooperate to form a spill-proof receptacle, and also serve to provide rigidity to the carrier.

In order to ensure that any spilled urine will be captured in the receptacle, the carrier is dimensioned so that the lower end of the collection bag extends into the receptacle when the bag is attached to the support hook. At the same time, it is desirable that the lower end of the bag does not contact the bottom wall to detach the bag from the support hook. Therefore, the carrier is also designed so that the bottom of the bag, while being within the receptacle, will also be spaced above the bottom wall.

In order to provide greater stability on horizontal surfaces, and in particular on non-rigid surfaces, such as carpet, the carrier also includes feet that project outwardly to the front and back of the carrier. Preferably, first and second feet, each with opposed ends that extend outwardly from the front and rear of the carrier, are positioned adjacent each side of the carrier along the bottom wall.

When used, a urine bag is inserted between side walls and the lower edge of the bag is positioned inside the receptacle. The hook is then inserted into the hook-receiving opening at the top of the bag. The user can then freely move about to conduct a variety of activities, setting the carrier on a horizontal surface at each of the destinations.

Thus, it is an aspect of the present invention to provide a moveable carrier for supporting a urine drainage bag that has a given width, a given height and a given filled thickness, comprising an open frame adapted to receive the bag; a hook for supporting the bag in the frame; a handle extending upwardly from the frame; and an open-top urine receptacle in the lower part of the frame, the bag extending partly into the receptacle when supported on the hook.

It is another aspect of the invention to provide a moveable carrier for supporting a urine drainage bag on a horizontal surface, the bag having a given width, a given height, a lower edge, and a given filled thickness, comprising a one-piece molded open frame adapted to receive the bag, the frame including a top wall with a lower surface, a bottom wall, first and second side walls, and front and back walls; a hook extending downward from the top wall lower surface to support the bag in the frame; a handle extending upwardly from the frame; and an open-top urine receptacle in the lower part of the frame, the receptacle being formed of the front, back, bottom and side walls, the bag extending partly into the receptacle when supported on the hook.

These and other aspects of the present invention will become apparent to one skilled in the art upon reading the detailed description of the invention that follows, taken together with the drawings.

DETAILED DESCRIPTION OF THE INVENTION

Figure 1:
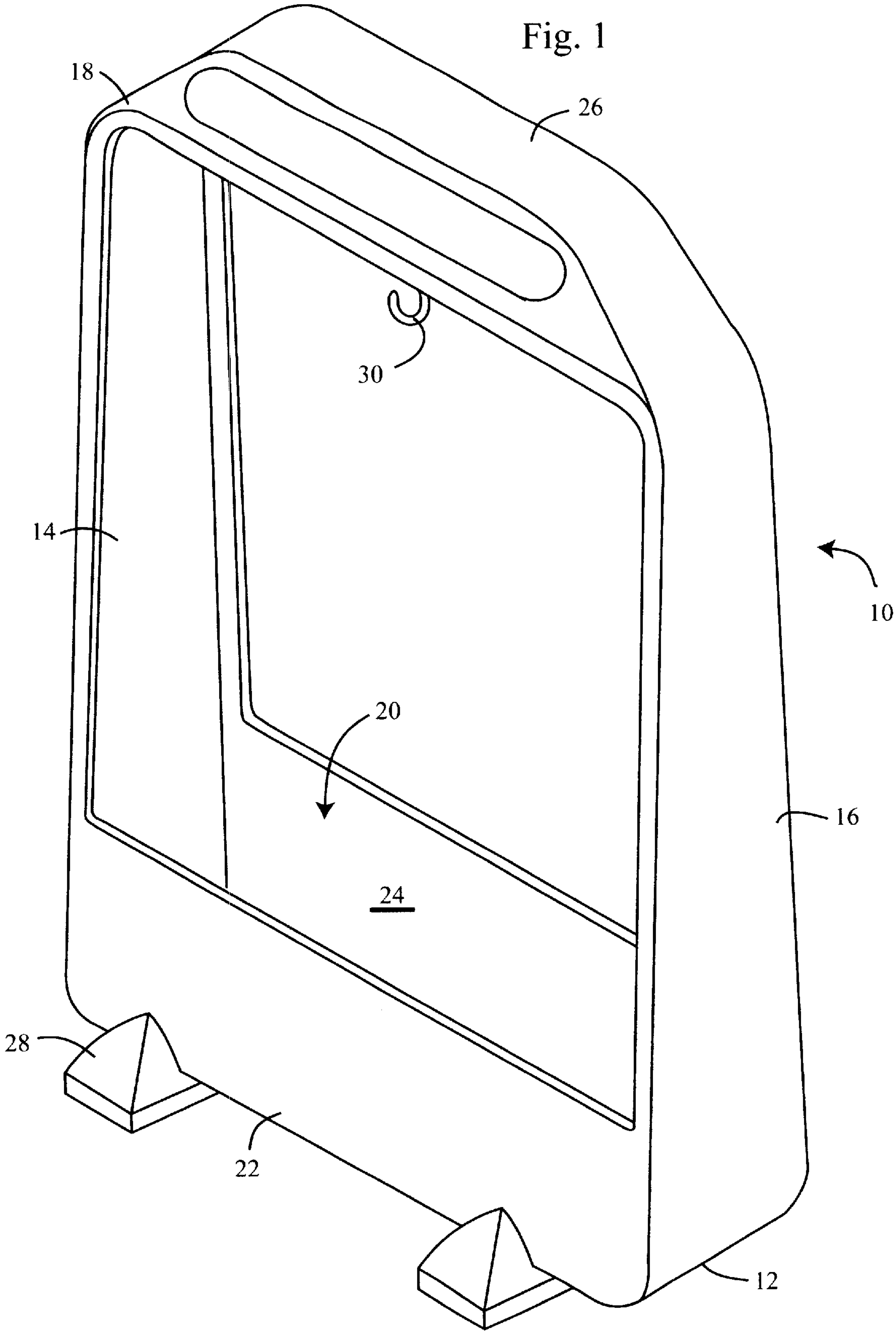
FIG. 1 is a perspective view of the carrier.

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

The drawings illustrate a preferred embodiment of a urine collection bag carrier, generally 10, that is comprised of an elongated horizontal bottom wall 12 having opposed ends and front and rear edges; elongated, identical first and second opposed side walls 14 and 16 having upper and lower edged and front and back side edges; and top wall 18 which also has opposed ends and front and rear edges. Walls 12, 14, 16, and 18 are integrally molded as a single piece, and together form a bag-receiving chamber that is open on both sides.

Carrier 10 includes a open-topped urine collection receptacle, shown at arrow 20, formed by walls 12, 14 and 16, and parallel front and back walls 22 and 24, that are also integrally molded with the other walls. Carrier 10 also includes handle 26 on the upper surface of wall 18, feet 28 extending to either side of wall 12, and a hook 30 that extends downward from top wall 18 and opens toward the front or back of the carrier.

Figure 2:
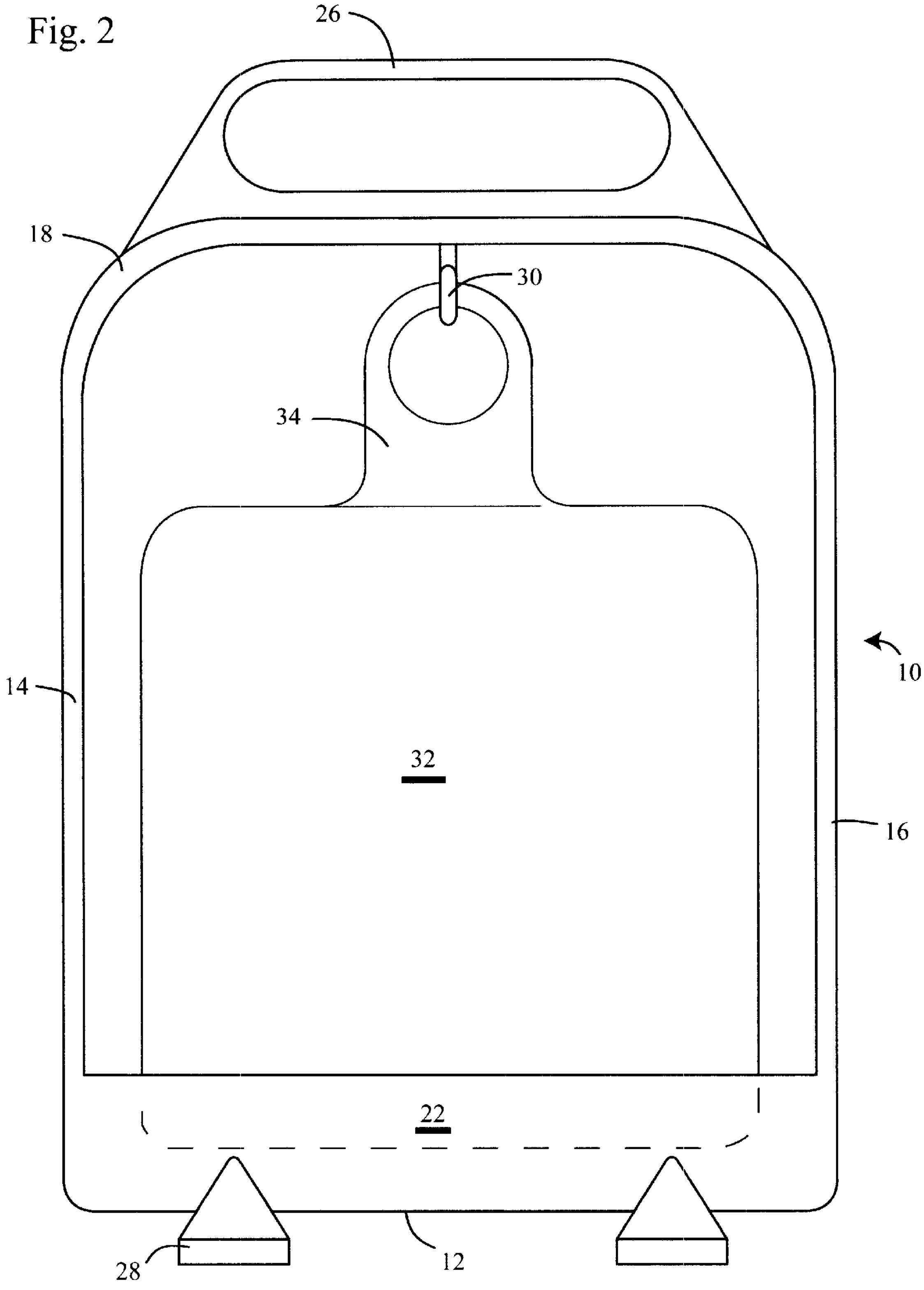
FIG. 2 is side view of the carrier with a urine bag supported within the carrier.
Figure 3:
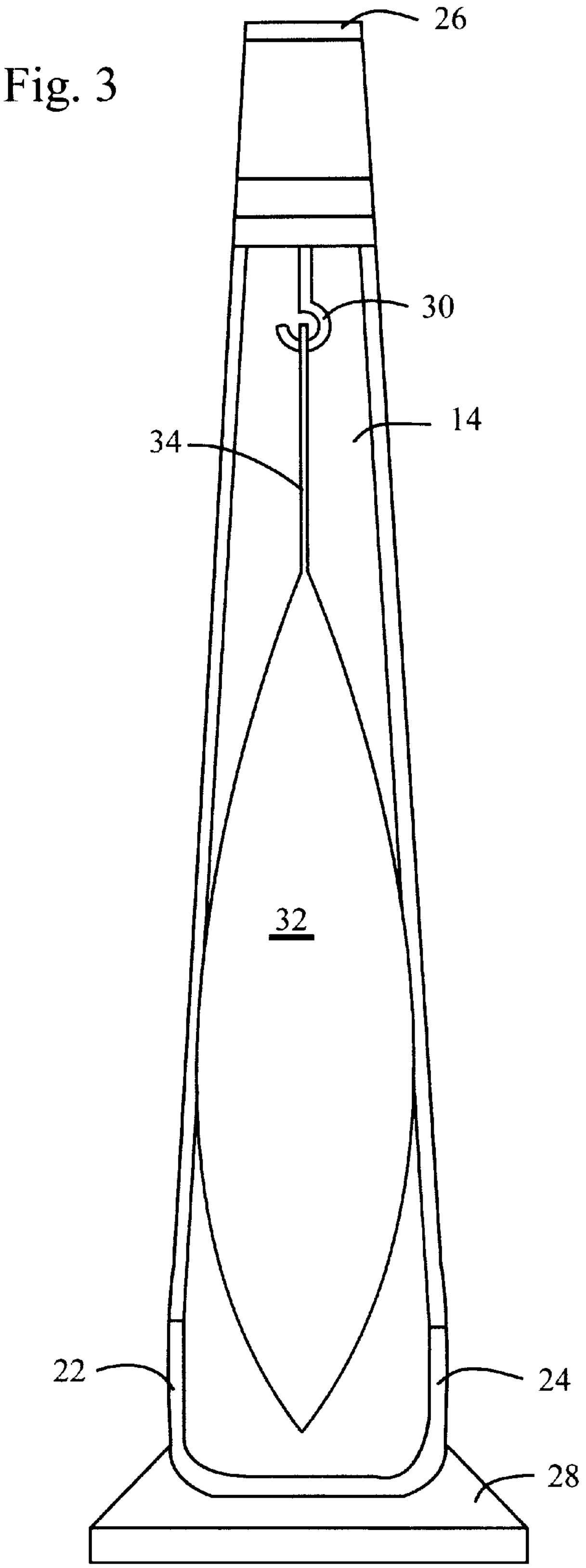
FIG. 3 is an sectional end view of one end of the carrier, both carrier ends being the same, showing a filled urine bag supported in the carrier.

Instead of requiring a specially designed bag, carrier 10 is sized and constructed to support standard urine bags of the type commonly used to hook onto bed rails. As shown in FIG. 2, carrier 10 to is sized to receive a representative rectangular urine collection bag 32, that includes an upper flap 34 with a hook receiving opening. Bag 32 has a width less than the distance between side walls 14 and 16, and a height such that the lower edge of bag 32 is spaced above bottom wall 12 when bag 32 is attached to hook 30. In order to prevent urine spillage, the lower end of bag 32 extends between front and back walls 22 and 24.

Certain modifications and improvements will occur to those skilled in the art upon a reading of the foregoing description. For example, the carrier as illustrated can be used with rounded urine drainage bags, or the carrier can be rounded to more closely approximate the shape of the bag. It should be understood that such modifications and improvements have been deleted herein for the sake of conciseness and readability but are properly within the scope of the follow claims.

What is claimed is:

1. A moveable carrier for supporting a urine drainage bag on a horizontal surface, said bag having a given width, a given height and a given filled thickness, comprising:

a) an open frame adapted to receive said bag, said frame including a top wall with an upper surface;

b) a bag support attachment for supporting said bag in said frame;

c) a handle extending upwardly from said frame top wall upper surface; and d) an open-top urine receptacle in the lower part of said frame, said bag extending partly into said receptacle when supported on said bag support attachment.

2. The carrier of claim 1, wherein said frame has a width at least equal to about the bag filled thickness.

3. The carrier of claim 1, wherein said open frame includes a top wall with a lower surface, and said bag support attachment is a hook extending downward from the center of said lower surface.

4. The carrier of claim 1, wherein said open frame includes a bottom wall, first and second side walls, and front and back walls, said bottom, side, front and back walls being integrally joined to from said urine receptacle.

5. The carrier of claim 1, further including support feet extending outwardly from opposite sides of said frame.

6. A moveable carrier for supporting a urine drainage bag on a horizontal surface, said bag having a given width, a given height, lower edge, ad a given filled thickness, comprising:

a) a one-piece molded open frame adapted to receive said bag, said frame including a top wall with a lower surface, a bottom wall, first and second side walls, and front and back walls;

b) a hook opening toward the front or back of said frame and extending downward from said top wall lower surface to support said bag in said frame;

c) a handle extending upwardly from said frame; and d) an open-top urine receptacle in the lower part of said frame, said receptacle being formed of said, back, bottom and side walls, said bag extending partly into said receptacle when supported on said hook.

7. The carrier of claim 6, wherein said handle is integrally molded with said top wall.

8. The carrier of claim 6, wherein said side walls are spaced at a distance greater than the given width of said urine drainage bag.

9. The carrier of claim 6, further including support feet integrally formed with said bottom wall.

10. The carrier of claim 6, wherein the lower edge of said bag is spaced above said bottom wall when said bag is supported on said bag support attachment.

11. The carrier of claim 6, wherein said side walls and said bottom wall have widths at least equal to about the given filled thickness of said urine drainage bag.

12. A moveable carrier for supporting a rectangular urine drainage bag on a horizontal surface, said bag having a given width, a given height, a upper and lower edges, a flap with a hook-receiving opening extending from said upper edge, and a given filled thickness, comprising:

a) a one-piece molded open frame adapted to receive said bag, said frame including a top wall with a lower surface, a bottom wall, first and second side walls, and front and back walls;

b) a hook extending downward from said top wall lower surface to support said bag in said frame;

c) a handle extending upwardly from said frame; and d) an open-top urine receptacle in the lower part of said frame, said receptacle being formed of said front, back, bottom and side walls, said bag extending partly into said receptacle with the lower edge of said bag spaced above said bottom wall when said bag is supported on said hook.

13. The carrier of claim 12, wherein said side walls and said bottom wall have widths at least equal to about the given filled thickness of said urine drainage bag.

14. The carrier of claim 12, wherein said side walls are spaced at a distance greater than the given width of said urine drainage bag.

15. The carrier of claim 12, further including support feet integrally formed with said bottom wall.

16. A moveable carrier for supporting a urine drainage bag on a horizontal surface, said bag having a given width, a given height and a given filled thickness, comprising:

a) a one-piece molded open frame adapted to receive said bag, said frame including a top wall with a lower surface, a bottom wall, first and second side walls, and front and back walls;

b) a hook opening toward the front or back of said frame and extending downward from said top wall lower surface to support said bag in said frame;

c) a handle extending upwardly from said frame; and d) an open-top urine receptacle in the lower part of said frame, said receptacle being formed of said front, back, bottom and side walls, said bag extending partly into said receptacle when supported on said hook, said side walls and said bottom wall have widths at least equal to about the given filled thickness of said urine drainage bag.

17. The carrier of claim 16, wherein said bag support attachment is a hook that opens toward the front or back of said frame.

18. The carrier of claim 16, wherein said handle is integrally molded with said top wall.

19. The carrier of claim 16, wherein said handle is integrally molded with said top wall.

20. The carrier of claim 17, further including support feet integrally formed with said bottom wall.

* * * * *